United States Patent [19]

Sammons et al.

[11] Patent Number: 5,439,571
[45] Date of Patent: Aug. 8, 1995

[54] APPARATUS AND METHOD FOR ENHANCED RESOLUTION CONTINUOUS FLOW ZONE ELECTROPHORESIS

[75] Inventors: David W. Sammons; Rizwan Sharnez, both of Tucson, Ariz.

[73] Assignee: Bioseparations, Inc., Tucson, Ariz.

[21] Appl. No.: 794,078

[22] Filed: Nov. 19, 1991

[51] Int. Cl.$^6$ .................. G01N 27/26; G01N 27/447
[52] U.S. Cl. ............... 204/180.1; 204/299 R; 204/301
[58] Field of Search ............ 204/299 R, 301, 180.1

[56] References Cited

FOREIGN PATENT DOCUMENTS

| 61-010758 | 1/1986 | Japan | 204/299 R |
| 552108 | 4/1977 | U.S.S.R. | 204/299 R |
| 1354093 | 11/1987 | U.S.S.R. | 204/299 R |

Primary Examiner—Kathryn Gorgos
Assistant Examiner—John S. Starsiak, Jr.
Attorney, Agent, or Firm—David G. Rosenbaum; Laura J. Zeman

[57] ABSTRACT

An apparatus and method of continuous flow zone electrophoresis for separation of particulates or biological samples, including cells and sub-cellular components, in a separation chamber configured to enhance separation of the sample components. The peak-to-peak distance between sample components in a non-equilibrium continuous flow zone electrophoretic fractionator is amplified by selective manipulation of particle residence time within the separation chamber.

25 Claims, 8 Drawing Sheets

APPARATUS AND METHOD FOR ENHANCED RESOLUTION CONTINUOUS FLOW ZONE ELECTROPHORESIS

STATEMENT OF GOVERNMENT INTEREST

This invention was made with Government support under Contract NAG8716 awarded by the National Aeronautics and Space Administration. The Government has certain rights in the invention.

BACKGROUND OF THE INVENTION

The present invention relates generally to the separation of biological samples in a fluid flow introduced into a separation chamber in the presence of an applied field. More particularly, the present invention presents an apparatus and method of continuous flow zone electrophoresis for separation of particulate materials or biological samples, including cells and sub-cellular components, in a separation chamber configured to enhance separation of the sample components. The foregoing is accomplished by amplifying peak-to-peak distance between sample components in a non-equilibrium continuous flow zone electrophoretic fractionator by selective manipulation of particle residence time. The fractionator is provided with an axial fraction collector and a positive gradient along the applied field in particle residence time and/or particle deflection rate.

In the approximately thirty years since its inception, continuous flow electrophoresis has emerged as a powerful method for separating cells and subcellular components. Because it is carrier free and gentle, continuous flow electrophoresis offers a fast and efficient alternative to centrifugation. In fact, since cellular function is more closely associated with surface charge than with volume or density, properties upon which centrifugation effectuates separation, continuous flow electrophoresis has greater potential for purifying functionally homogeneous cell populations. Moreover, because functional activity is substantially preserved and samples are efficiently recovered, continuous flow electrophoresis is particularly attractive for large scale purification.

Barriolier, V. J., et al, *Z. Naturforsch,* 136:754 (1958) were the first group to reduce a continuous flow electrophoretic fractionator to purify biomolecules. The technique was further refined by Hannig, K., *Z. Anal. Chem.* 181:244–254 (1961) and Strickler, A., et al, *Annals N.Y. Acad. of Sci.,* 209:497–514 (1973). Early applications of continuous flow electrophoresis were restricted to the separation of soluble components such as proteins and other biomolecules; the technology was extended to cells and subcellular components. Hjerten, S., *Cell Separation Methods,* Amsterdam, The Netherlands: Elsevier/North-Holland Biomedical Press, B.V., Bloemendal, H., ed., 127 (1977).

The principal of continuous flow electrophoresis entails establishing a conveying buffer flow in a first direction, either upwards or downwards, relative to gravity, in a narrow gap between two flat parallel plates. A sample is injected into the buffer at the center of the gap as a stream. The sample typically contains charged sub-populations A and B. The elements of A have a greater surface charge density ($\sigma$), and, therefore, a greater mobility ($\mu$), than those of B. Thus, $\sigma_A > \sigma_B$, and $\mu_A > \mu_B$. As the elements of A and B are conveyed by the buffer along an axial direction Z, they migrate towards the oppositely charged electrode, i.e., negatively charged components will migrate toward the anode. Since $\mu_A > \mu_B$, the elements of A migrate faster than the elements of B. Consequently, by the time the sample reaches the end of the chamber, the elements of A and B are separated by some peak to peak distance $\delta_{AB}$. The separated sample components are collected by a fraction collector.

An inherent limitation of continuous flow electrophoresis in the currently available apparatus and methods, is that the peak to peak distance ($\delta_{AB}$) is often too small to fractionate the sample into substantially biologically pure components. It has been found that this is due to i) the sub-populations of most biological samples differ minutely in charge density; ii) the fraction collector exit receptacle must have an internal diameter of at least 0.5 mm to avoid obstruction and non-uniform flow; iii) the deflection of the sample towards the anode or cathode, which determines $\delta_{AB}$, must be on the order of a 1 cm separation to maintain stable flow; and iv) the finite size of the injection tube and the dispersion of the sample during electrophoresis typically lead to overlapping peaks.

The inventors have found that with the current state of continuous flow electrophoresis, particles can be effectively fractionated only if their relative mobilities differ by at least 10%. The degree to which mobilities of the particles limit sensitivity of the continuous flow electrophoresis can be estimated by expressing the sensitivity (S) in terms of the smallest mobility interval $\Delta\mu = (\mu_A - \mu_B)$ that can be fractionated into pure components A and B. Assuming that $\delta_{AB}$ must be at least twice the diameter of the receptacle, i.e., $\delta_{AB}$ must be greater than or equal to $2\Delta = 1$ mm, to isolate A from B without unacceptable overlap, then S may be expressed as:

$$S = (\mu_A - \mu_B)_{min} = (\Delta\mu)_{min} \text{ for which } \delta = 1 \text{ mm}$$

To evaluate the S, the relationship between $\delta_{AB}$ and $\Delta\mu/\mu$ is derived. By definition of particle mobility $\mu$, the average net deflection (D) of the sample from the axis of introduction in a given Y-Z plane is related to the applied field strength (E) and the net residence-time ($\tau$) of the sample in that plane, by the following equation:

$$D = \mu E \tau$$

where $\mu = (\mu_A - \mu_B)/2$ is the average net mobility of the sample.

Similarly, the average net deflection of the two sample components $D_A$ and $D_B$ are:

$$D_A = \mu_A E \tau$$

$$D_B = \mu_A E \tau$$

Thus, the peak to peak distance between sample components $\delta_{AB}$ may be expressed as:

$$\delta_{AB} = D_A - D_B = (\mu_A - \mu_B) E \tau = \Delta\mu E \tau$$

substituting for $E \tau$ gives:

$$\delta_{AB} = (\Delta\mu/\mu)D, \text{ or } \Delta\mu/\mu = \delta_{AB}/D$$

substituting for $\Delta\mu/\mu$ for $\delta = 1$ mm, we get:

$$s = (\Delta\mu/\mu)_{min} = 1/D_{max}$$

where $D_{max}$ is the maximum possible deflection of the sample components. It has been found that, under terrestrial conditions, D has to be on the order of 1 cm to maintain stable flow, assuming $\mu$ to be approximately 1 $\mu$m/sec per V/cm of applied field. Thus, $(\Delta\mu/\mu)_{min}$ must be on the order of 0.1 or 10%, an estimate which compares well with published values.

The 10% variance in relative component mobility can sometimes be overcome by selectively altering the surface charge of a sub-population via chemical modification of the surface groups. However, this approach requires that specific strategies must be developed on a case by case basis and may lead to changes in functional activity.

Resolution in continuous flow electrophoresis is also limited by wall effects such as electroosmosis and transverse gradients in sample residence time and temperature. The combination of these factors leads to the well-known crescent effect. While the crescent effect may be partially controlled by manipulating electroosmosis, this approach has limited applicability where the flow velocity profile deviates from the ideal parabolic transverse shape. Such deviations are more problematic under terrestrial conditions where buoyancy driven phenomena, such as thermal convection and particle and zone sedimentation are significant.

The problem of temperature variation is also important in scaling up continuous flow electrophoresis. It is known that a 17° C. temperature differential exists between the wall and center of a 0.5 cm thick chamber, even where both walls of the chamber were cooled. Saville, D. A., *PCH Physico Chemical Hydrodynamics*, 1:299 (1980). Since particle mobility increases about 3% per degree centigrade (Hannig, K., et al, *Biochemistry and Diagnostics*, Git Verlag, GMBH, 93 (1990)) flow band broadening would result from such a temperature drop. Thermal convection also seriously limits scaling up of continuous flow electrophoresis. Efficient heat removal is not feasible if chamber thickness exceeds 1 mm.

Particle and zone sedimentation are two other buoyancy-induced phenomena that affect separation resolution and scale up potential. Particle sedimentation can lead to artifactual broadening of bands where particle size is on the order of 1 $\mu$m or more, whereas zone sedimentation limits concentration of the sample stream.

Under microgravity, however, particle and zone sedimentation cease to be limiting. However, secondary field effects such as ohmic heating and electrohydrodynamics become limiting. Peeters, H., *Cell Separation Methods*, Amsterdam, The Netherlands: Elsevier/North-Holland Biomedical Press, B.V., Bloemendal, H., ed., 162 (1977). In this case, the lack of buoyancy induced convection and poor thermal conductivity of the buffer lead to sample overheating. Saville, supra, demonstrated that, under typical operating conditions, the gap width of a separation chamber cannot be increased over 0.75 cm without overheating the sample.

Ohmic heating poses a limitation on the ionic strength of the buffer since heat generated by the electric field increases with conductivity of the buffer, and therefore with the ionic strength of the buffer. The need to minimize ohmic heating limits the factors of sample concentration and residence time.

Electrohydrodynamics degrades resolution through deformation of the sample stream. Rhodes, P. H., et al, *J. Colloid. Interface Science*, 129(1):90 (1989). The degree of sample deformation varies with the ratio of sample to buffer conductivity. Thus, sample concentration is directly limited and sample throughput is compromised.

Early attempts to amplify peak to peak distance were restricted to batch processes, such as those described by Biggin in 1983 or Ansorge in 1984, with buffer gradient and wedge shaped gels, respectively. The only known attempts at amplifying peak to peak distance in continuously operated fractionators has been achieved by selective manipulation of the surface-charge of the sub-populations through chemical modification of the surface groups.

The present invention achieves amplification of peak to peak distance by selectively manipulating particle residence-time and/or particle deflection rate. This approach has not heretofore been reported.

SUMMARY OF THE INVENTION

In accordance with a broad aspect of the invention, the present invention provides a method for enhancement of separation resolution in a continuous flow zone electrophoretic modality. Resolution enhancement is accomplished by selectively manipulating particle residence-time within the electrophoresis to permit the more highly mobile sub-population to separate from the relatively lesser mobile sub-population, thereby amplifying the peak-to-peak distance between elution of the sub-populations.

Selective manipulation of residence time is accomplished by any of i) reorienting the fraction collector; ii) decelerating the fluid in the direction of the applied field; iii) accelerating particle or sub-population deflection in the direction of the applied field; or iv) extending a post-electrode region.

These and other objects, features and advantages of the present invention will be more apparent to those skilled in the art from the following more detailed description of the preferred embodiments of the invention taken with reference to the accompanying Figures, in which like features are identified by like reference numerals.

BRIEF DESCRIPTION OF THE FIGURES

FIG. 15b is a cross-sectional view taken along line 15b–15b of FIG. 15a.

FIG. 15c is a cross-sectional view taken along line 15c–15c of FIG. 15a.

FIG. 16 is a diagrammatic view of the modified continuous flow zone electrophoresis apparatus shown in FIG. 15a.

DETAILED DESCRIPTION OF THE PREFERRED EMBODIMENTS

Figure 1:
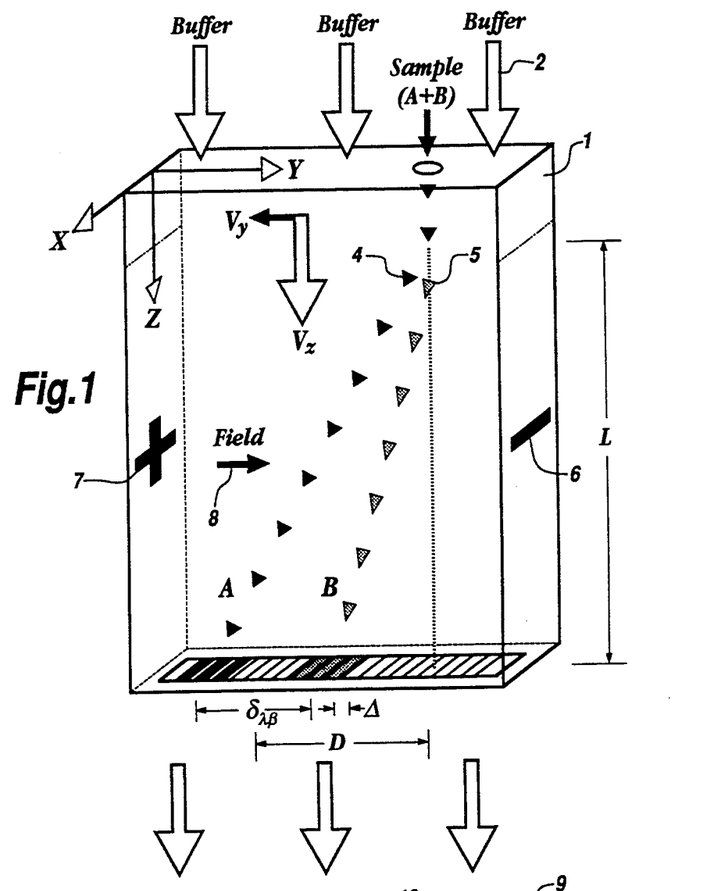
FIG. 1 is a perspective diagrammatic view of a prior art continuous flow zone electrophoretic chamber illustrating the principal of continuous flow electrophoresis relative to two sub-populations A and B in a sample of A+B.

The principles underlying continuous flow zone electrophoresis, and a typical apparatus, is illustrated in FIG. 1. A separation chamber 1 is provided which has X, Y and Z axes. The chamber 1 is defined by two flat parallel plates separated to form a gap, defining the X axis, and two electrodes, a cathode 6 and anode 7. The plates have a width, defining the Y axis, and a length, defining the Z axis. A conveying buffer 2 is flowed into the chamber 1 at a point on the Y axis, the flow being oriented in a first direction, such as in the Z-axis. A sample 3 is introduced into the buffer 2, either as a stream or as a pulsed injection. The sample 3 contains charged sub-populations A or 4, and B or 5. The elements of A have a greater charge density, $\sigma$, than those of B, i.e., $\sigma_A > \sigma_B$. In the presence of an applied electrical field 8, generated between cathode 6 and anode 7, the elements of A and B will migrate toward the oppositely charged electrode. As the elements of A and B are conveyed by buffer 2 in the axial direction or Z axis, A migrates toward the oppositely charged electrode at a faster rate than B. By the time the sample reaches the end of the chamber, A and B are separated by some peak-to-peak distance $\delta_{AB}$, have moved a lateral distance or deflection D from the axis of the point of sample introduction and traversed a length of the chamber L. The velocity of the Y axis is denominated $V_y$ and the velocity in the Z axis is denominated $V_z$. The separated sample-components are collected by a fraction collector, as is known in the art, at the base of the chamber 1.

As noted above, an inherent limitation of conventional continuous flow zone electrophoretic devices is that the peak-to-peak distance $\delta_{AB}$ is often too small to effectively fractionate the sample into substantially biologically pure samples. Current limitations on $\delta_{AB}$ are i) sub-populations of most biological samples differ minutely in their charge-densities; ii) the fraction collector receptacles must be at least 1 mm to avoid obstruction and non-uniform flow; and iii) the deflection D of the sample must be less than 15 mm to maintain stable sample/buffer flow.

In accordance with the preferred embodiments of the invention, there is provided a method which selectively manipulates residence time of the sample in the chamber by at least one of i) reorienting the fraction collector; ii) decelerating the fluid in the direction of the applied field; iii) accelerating particle or sub-population deflection in the direction of the applied field; or iv) extending a post-electrode region.

Figures 2, 3, 4:
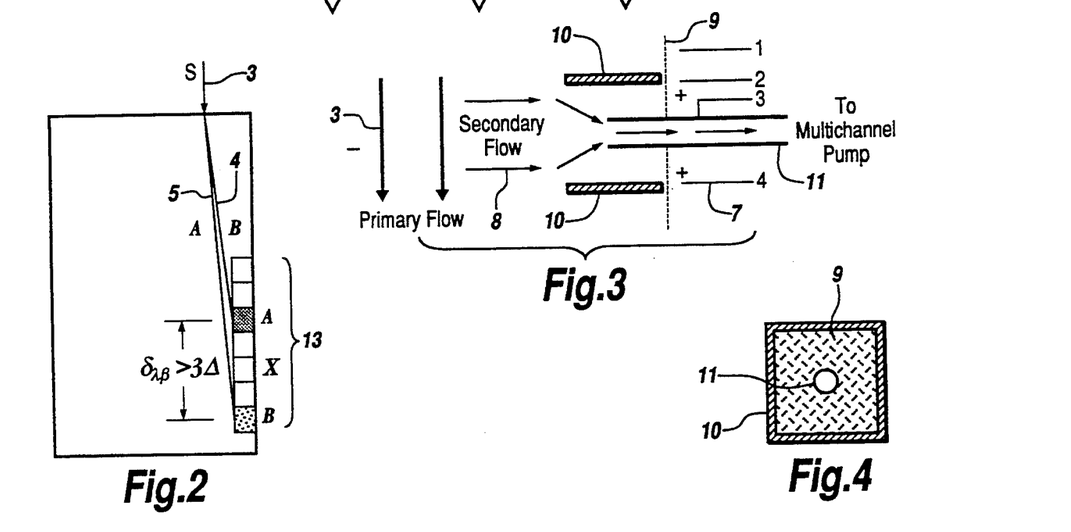
FIG. 2 is a diagrammatic view of the modified continuous flow electrophoresis chamber and fraction collector in accordance with the present invention.
FIG. 3 is a side elevational diagrammatic view of a fraction collection port of the modified continuous flow electrophoresis chamber of the present invention.
FIG. 4 is a diagrammatic cross-sectional view taken along line 4—4 of FIG. 3.

The peak-to-peak distance $\delta_{AB}$ may be enhanced by reorienting the fraction collector to an axial direction relative to the sample flow. FIG. 2 illustrates fraction collector 13 positioned in the Z axis of the chamber, and thus, axial to the direction of the sample flow. In this position the residence time of the slower sub-population B, $\tau_B$, is extended relative to that of the faster sub-population A, $\tau_A$, thereby enhancing peak-to-peak distance $\delta_{AB}$. While this adaptation is effective in amplifying peak-to-peak distance $\delta_{AB}$, adjusting the angle of inclination of the fraction collector between 0° and 90° from the axis of the chamber 1 will extend the residence time of both A and B, and further enhance the resolution or peak-to-peak distance.

FIGS. 3 and 4 illustrate an embodiment of an axial fraction collector in accordance with the present invention. Sample flow 3 is directed in a first or axial direction. The secondary flow or migration of particles in sub-populations A and B caused by field 8 directs A and B toward the side wall of the chamber. At the side wall of the chamber there is provided an ion-exchange membrane 9 and a series or receptacles 10 which collect fractions eluting at the position of the receptacle 10 along the direction of the sample flow 3. The receptacles 10 communicate a collected fraction to a fluid conduit 11, which passes through the ion-exchange membrane 9, in fluid flow communication with a multichannel pump (not shown). In this manner, a purified sample eluting at an axial position corresponding to a given receptacle 10 may be collected.

Figure 5:
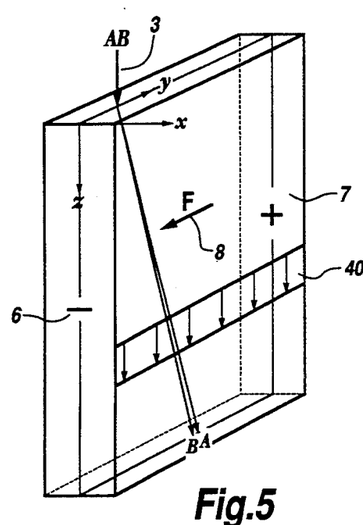
FIG. 5 is a diagrammatic perspective view of a conventional continuous flow electrophoretic chamber illustrating flow profile through the chamber upstream from a conventional fraction collector.
Figure 6:
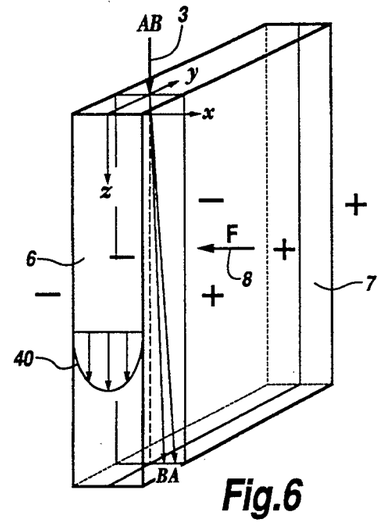
FIG. 6 is a diagrammatic perspective view of a modified chamber illustrating re-orientation of the electrodes upstream from a conventional fraction collector.

A second method for enhancing resolution, and therefore, sensitivity of continuous flow zone electrophoresis, is to increase the residence time of A relative to B such that $\tau_A > \tau_B$ upstream from the fraction collector. This may be accomplished by decelerating the fluid along the direction of the applied field 8, or in the direction of the deflection D. This is illustrated with reference to FIGS. 5 and 6. FIG. 5 illustrates a conventional continuous flow zone electrophoresis chamber in which the flow velocity-profile 40 along the direction of the field is flat. Under these conditions, the residence time of a particle is independent of its mobility or its charge-density. Thus, no matter how fast the particle deflects along the Y axis, i.e., $V_y$, its velocity along the Z axis, $V_z$, remains constant. Thus, both sub-populations have substantially identical residence times, i.e., $\tau_A = \tau_B$. However, if, as illustrated in FIG. 6, the field is re-oriented to the x-axis of the chamber by associating the electrodes 6,7 with the walls of the chamber, the applied field 8 is directed from one wall to the other. In this configuration, the residence time $\tau$ of a particle is dependent upon its mobility m because of the parabolic flow velocity profile 40. Where A and B are injected as sample 3 at a point along the Y axis of the chamber 1, and $m_A > m_B$, the elements of A are always closer to the anode 7 than those of B. The parabolic flow velocity profile 40 will, therefore, have a smaller mean Z-axis velocity relative to B. A will, therefore, have a greater residence time in the field relative to B. Thus, for the same applied field strength 8 and average sample residence time $\tau$, the peak-to-peak distance $\delta_{AB}$ increases. Application of the electric field 8 across the chamber gap deflects the sample from a region of higher fluid velocity to an area of lower fluid velocity, therefore amplifying $\delta_{AB}$ and enhancing separation sensitivity.

Figure 7:
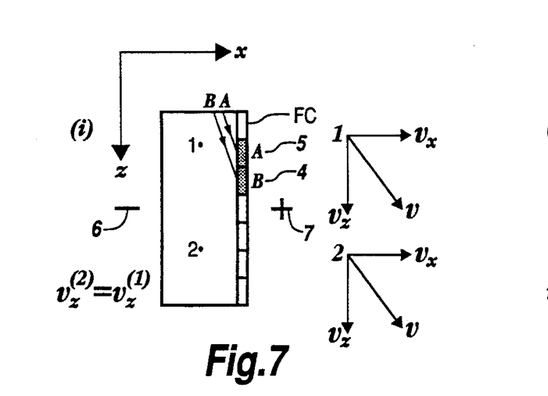
FIG. 7 is a diagrammatic view of a modified continuous flow electrophoretic chamber illustrating flow profile downstream the chamber at the modified fraction collector of the present invention.
Figure 8:
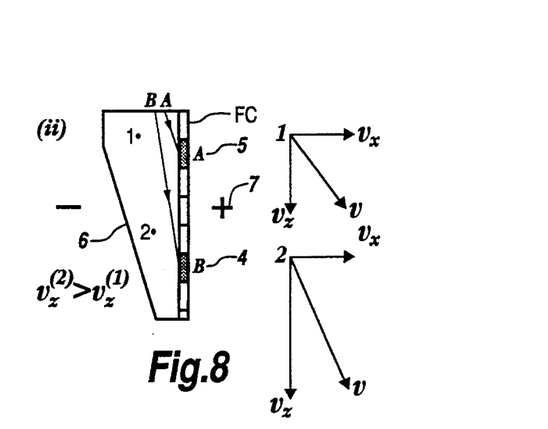
FIG. 8 is a perspective diagrammatic view of a modified fraction collector section illustrating the improved separation method in accordance with the present invention.

The axial velocity of the fluid downstream the fractionator may be enhanced by tapering the cathode. FIG. 7 illustrates the situation in which there are parallel electrodes and no enhancement of residence time due to increase in the axial fluid velocity. FIG. 8, however, illustrates that a tapered electrode, in this case cathode 6, narrows the separation chamber, thereby compressing the fluid velocity flow profile toward the end of the chamber and increasing the residence time of the slower B component in the fluid flow.

Figure 9:
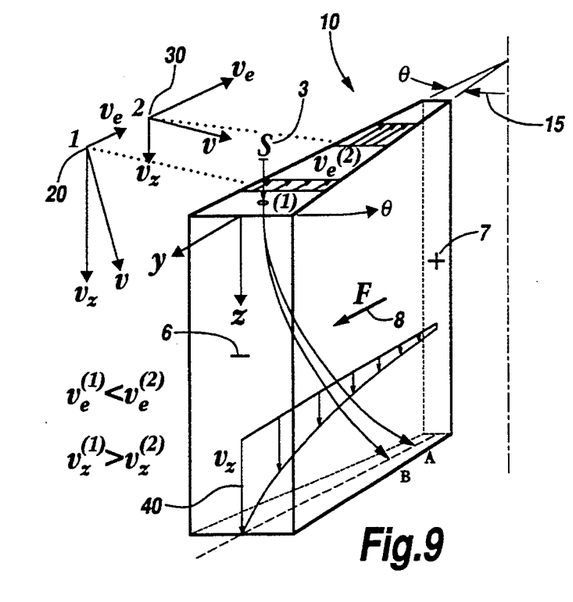
FIG. 9 is a diagrammatic view of a modified chamber illustrating sample separation.
Figure 14A:
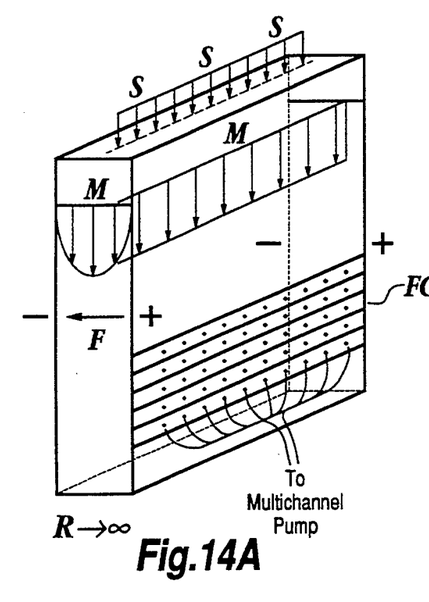
FIG. 14a is a perspective view of a first configuration of the modified continuous flow zone electrophoresis chamber in a flat plate parallel configuration of the chamber side walls in accordance with the present invention.
Figure 14B:
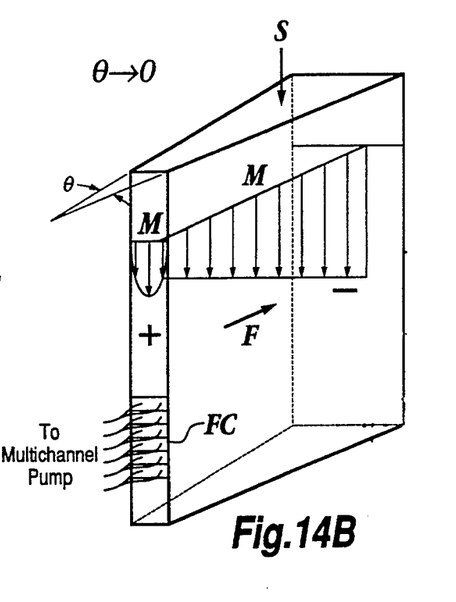
FIG. 14b is a perspective view of a second configuration of the modified continuous flow zone electrophoresis chamber in a flat plate tapered chamber configuration in accordance with the present invention.

A third method for enhancing resolution in continuous flow zone electrophoresis is to accelerate a particle along the field. Ordinarily, the deflection rate, or net velocity of a particle, is independent of its spacial coordinates in the chamber. However, as illustrated in FIG. 9, the rate of deflection may be increased by forcing the particle to enter regions of lower fluid velocity at a faster rate. This is accomplished by providing a chamber having angularly displaced walls. The walls of the chamber taper at an angle $\theta$ forming a wedge-shaped or tapered chamber. The chamber walls taper towards the anode 7 so that the fluid flow velocity profile is compressed as the fluid flow approaches the anode 7. This effect can be achieved through a radial gradient in any parameter which determines the deflection rate of a particle, i.e., gap-width, as illustrated in FIG. 9, viscosity, ionic-strength, temperature, etc. Compression of the Z-axis velocity profile 40 results in forcing the particle toward the chamber wall, and closer to the regions of lower fluid velocity, thereby slowing of the sample components A and B. Vector diagrams 20 and 30 illustrate fluid velocity in the Z-axis, $V_Z$, electric field in the Y axis, $V_e$, and the relative velocity and direction of the sub-populations in the chamber, V, affected by the fluid velocity and the electric field, measured at points 1 and 2. At point 1, sample mobility is primarily under the influence of the fluid velocity $V_Z$ and exposed to a smaller field gradient $V_e$. However, moving along the Y axis to point 2, the sub-populations are moved to an area of slower fluid velocity $V_Z$, imparted by wall effects, and into an area of higher field gradient $V_e$, due to the decreased buffer volume. FIG. 14b is illustrative of the wall effect on fluid velocity profile through the wedge-shaped or tapered chamber, and illustrates coordination between the axially disposed fraction collector and the tapered chamber in accordance with the invention. Accordingly, the tapered chamber 10 exposes the sample sub-populations to slower fluid flow and increased field strength as the sub-populations approach the electrode. In this manner the residence time of the faster component $\tau_A$ is increased relative to that of the slower component $\tau_B$ and $\delta_{AB}$ is increased.

Figure 10:
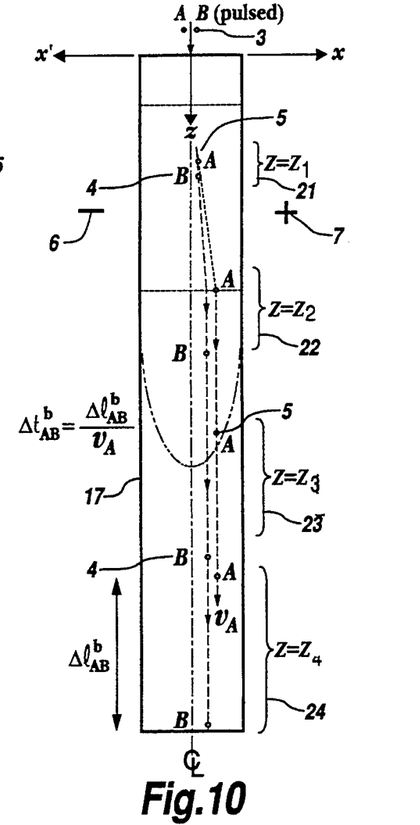
FIG. 10 is a diagrammatic view of pulsed sample injection separating sample components A and B along a time-coordinate with an extended post electrode region.

Finally, a fourth method for selectively manipulating the residence time of a particle is to extend the post-electrode region of the separation chamber and pulse inject the sample into the separation chamber. FIG. 10 illustrates an extended post electrode region 17 and the effect of the extended post electrode region 17 on the relative flow velocities of sub-populations A and B. The sample 3, containing sub-populations A and B, is pulse injected into the buffer flow. Upon injection of a single pulse, A and B separate in accordance with their relative mobilities in the applied field 8 between electrodes 6 and 7. Because the sample migrates across a negative velocity gradient imposed by the parabolic flow velocity profile between the electrodes 6 and 7, the faster component A moves closer to the wall, enters the region of the slower velocity profile and assumes a slower axial velocity $V_z$ than the slower component B. Additionally, because the sample 3 is pulse injected, sequential fractions become separated not only along the spacial x and z axes, but also along the time axis. Because of the sequential pulse injection, the separated fractions must be sequentially collected in time, rather than in space. Thus, the sensitivity of the separation is proportional to the time-interval $\Delta t_{AB}$ between the emergence of A and B, instead of the peak-to-peak distance $\delta_{AB}$. Sensitivity can be enhanced by increasing $\Delta t_{AB}$. This may be accomplished by extending the length of the post electrode region into sequential $Z_1$, $Z_2$, $Z_3$ and $Z_4$ regions, 21–14, respectively. For a known time interval $\Delta t^\circ_{AB}$ before the extended post electrode region, the $\Delta t_{AB}$ after extension by a length L is expressed as:

$$\Delta t_{AB} = L/V_A - (L - [\Delta t^\circ_{AB} V_B])/V_B$$

where $V_A$ and $V_B$ are the steady velocities of A and B.

With the exception of the first and fourth above described methodologies, which require different sample input methods, most of the methods can be used in combination synergistically to increase residence time $\tau$ of the sub-populations.

Figure 11A:
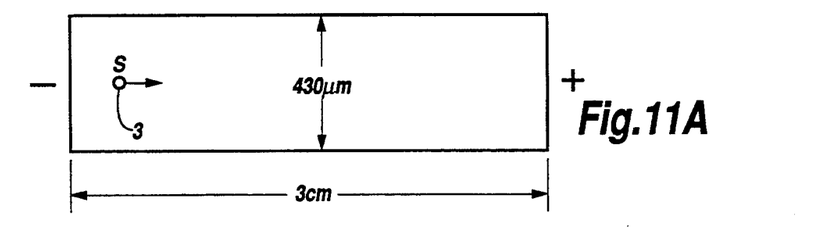
FIG. 11a is a cross-sectional view of a conventional continuous flow zone electrophoresis chamber.
Figure 11B:
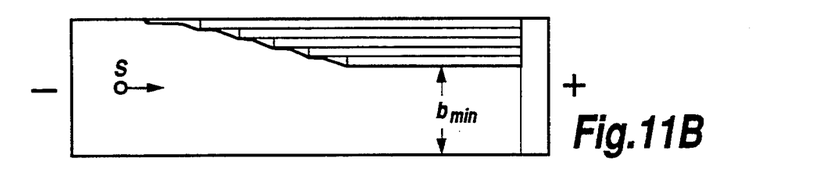
FIG. 11b is a cross-sectional view of a modified continuous flow zone electrophoresis chamber.
Figure 12:
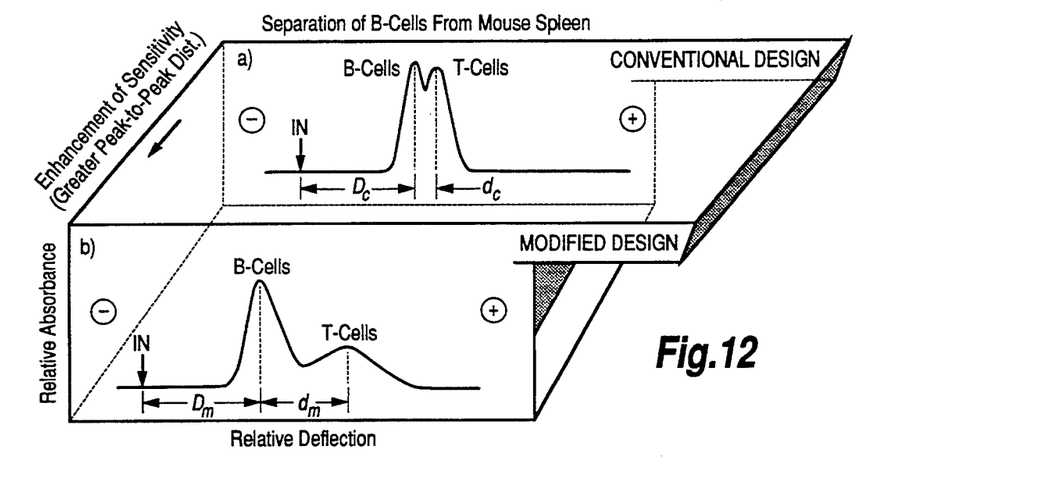
FIG. 12 is a graph comparing resolution of the conventional and modified continuous flow zone electrophoresis chambers of FIGS. 11a and 11b used for separation of B-cells and T-cells from a single sample.
Figure 13:
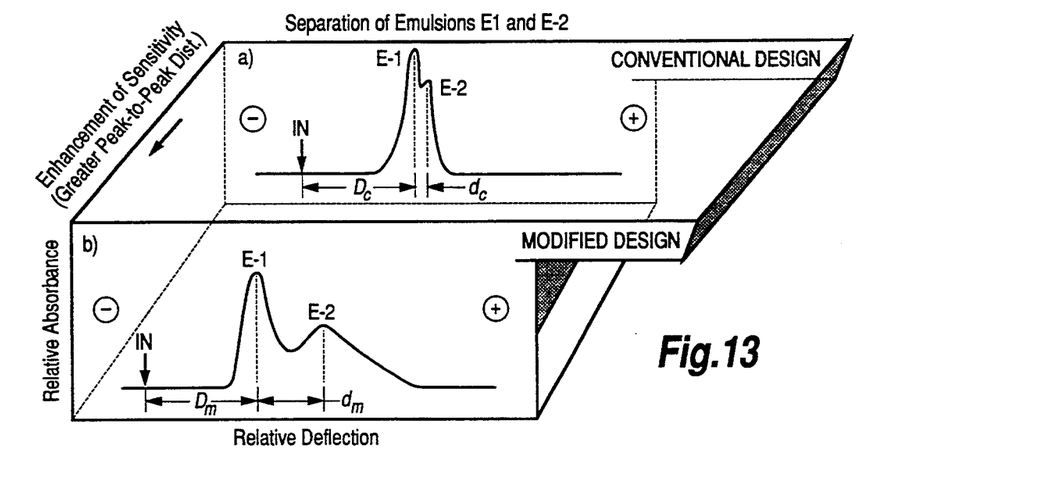
FIG. 13 is a graph comparing resolution of the conventional and modified continuous flow zone electrophoresis chambers of FIGS. 11a and 11b used for separation of emulsions.

The following examples are illustrative of the operation of the modified tapered chamber design in accordance with the present invention. In both examples a tapered chamber was made from a conventional parallel plate continuous flow zone electrophoresis chamber by modifying its cross-sectional profile. FIG. 11a illustrates a conventional chamber having a uniform gap width of 430 μm, and FIG. 11b illustrates the modified chamber having a tapered gap width with a minimum width of 230 μm. The taper was simulated as a series of step changes in gap thickness. The steps were made out of a water based adhesive material approximately 25μ in thickness. To smooth the edges, the steps were covered with a single sheet of the adhesive material. The sample was injected a sufficient distance from the entrance to the tapered section to avoid the flow transition zone. The entrance length was estimated from a simplified form of the Navier-Stokes Equation for flow of a Newtonian liquid in a slit. In the modified chamber of FIG. 11b, the axial velocity $V_Z$ of the fluid varied approximately with the square of the gap width. Thus, the particle residence time $\tau$ varied sharply along the direction of the field, being much greater at the narrower end than it was at the wider end. Another characteristic of the modified chamber was that the field strength, and therefore the deflection rate, varied inversely with the gap width. The resulting acceleration of the particle as it migrated towards the anode enhanced the effect of the residence time gradient.

EXAMPLE 1

A conventional parallel plate continuous flow zone electrophoresis chamber depicted in FIG. 11a and a modified tapered chamber depicted in Figure b were employed. The chamber buffer composition in both chambers was 15 mM TEA, 4 mM potassium acetate, 240 ml glycine and 11 mM glucose. The electrode buffers were 75 mM TEA and 20 mM potassium acetate. The pH was adjusted to 7.2 with glacial acetic acid. The electrical conductivities of the chamber and electrode buffers were 1100 and 5400μ mhos/cm, respectively. The buffer curtain had an average velocity of 2 cm/sec. The field strength was 177 V/cm, and current was 75 mA.

Sample migration was from the cathode to the anode, and the deflection of the slower B-cell component was the same in both the conventional and the modified chamber, whereas the peak-to-peak distance between the B-cell component and the faster T-cell component increased by a factor of four with the modified design. Elution of the faster T-cell component was delayed by the increased residence time $\tau$ of the T-cell component in the modified chamber of the present invention.

EXAMPLE 2

The same protocol was followed as in Example 1 above, except that the two components in the sample were emulsions E1 and E2, and the field strength was 79 V/cm and the current was 29 mA. Again, the deflection of the slower component E1 was the same in both the conventional and modified chambers, the deflection of the faster component E2 was delayed, increasing the peak to peak distance by a factor of five.

The experimental results closely agree with calculated values. For a conventional chamber, as illustrated in FIG. 11a, of rectangular cross-section, $\delta_{AB}$ is given by:

$$\delta = D_A - D_B = (\mu_A - \mu_B)/\mu D = \Delta\mu/\mu D = kD$$

where $\mu_A$ and $\mu_B$ are the mobilities of the two sub-populations being separated, $\Delta\mu/\mu D = k D$ is a constant for a given sample and buffer, and D is the average net deflection of the sample.

For a tapered chamber, the peak to peak distance $\delta'$ for the same average net sample deflection D over N equal steps of width D/N is given by:

$$\delta' = \frac{\Delta\mu}{\mu} \; \frac{D}{N} \sum_{N-1}^{i=1} (b_i/b_N)^3$$

since $(\Delta\mu/\mu) D = \delta$, and $\delta'/\delta$ is the amplification A, thus, $$A = \left(\frac{\delta'}{\delta}\right) = \frac{1}{N} \sum_{N-1}^{i=1} (b_i/b_N)^3$$

Where the prime indicates that the chamber is tapered, and $b_i$ is the thickness of the chamber at step i. Substituting the values of $b_i$, A=4.2 is calculated for Example 1 and A=5.5 for Example 2, calculated results which closely parallel the experimental data.

Thus, the results of the Examples demonstrates that in the modified continuous flow electrophoretic chamber of the present invention, the peak-to-peak distance between the sample components can be selectively enhanced by increasing the residence time of the faster component and decreasing the residence time of the slower component.

Figure 14C:
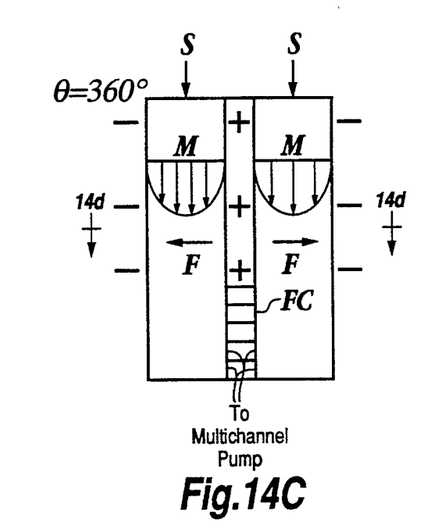
FIG. 14c is a side elevational cross-sectional view of a third configuration of the modified continuous flow zone electrophoresis chamber illustrating the annular chamber configuration in accordance with the present invention.
Figure 14D:
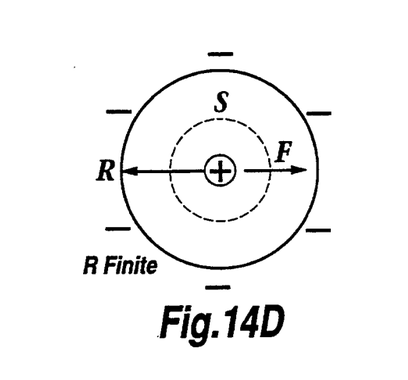
FIG. 14d is a cross-sectional view taken along line 14d—14d of 14c.

The above-described tapered chamber is only one of numerous chamber designs which exploit the above method to enhance separation sensitivity and resolution. Indeed, as illustrated in FIGS. 14a-d, alternative chamber configurations, all of which embody the described methodologies, are regarded as within the scope of the present invention. Specifically, the feature of selective enhancement of residence time of the faster sample component is achievable with a parallel plate, in a transverse gap electric field, coupled to a fraction collector as illustrated in FIG. 14a, or in the tapered chamber, coupled to a fraction collector, as illustrated in FIG. 14b, or in an annular chamber, as illustrated in FIGS. 14c-d, in which the fraction collector resides within the central annulus of the chamber, and the applied field, and hence deflection, is radial to the annular chamber. Those skilled in the art will note that the annular chamber depicted in FIGS. 14c-d is merely a modification of the tapered chamber design noted in FIG. 14b and described above, except that $\theta = 360°$.

Figure 15A:
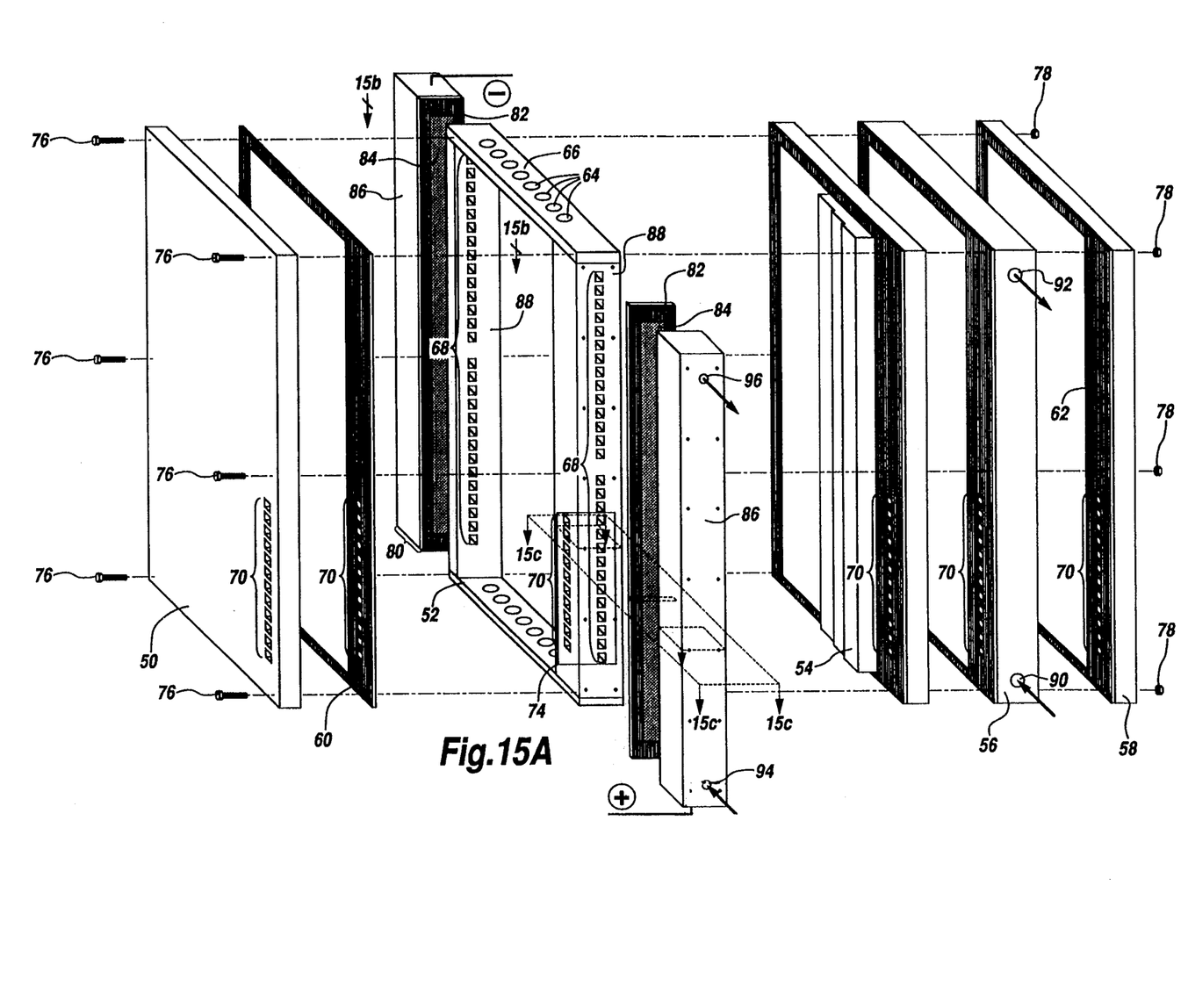
FIG. 15a is a perspective exploded view of a modified continuous flow zone electrophoresis apparatus containing the second embodiment of the electrophoresis chamber comprising a flat plate tapered chamber as shown in FIG. 14b.

FIG. 15a illustrates a modified flow zone electrophoresis apparatus having an electrophoresis chamber which comprises a flat plate tapered chamber configuration. The apparatus comprises a front end plate 50, a separation chamber which is defined by a separation chamber spacer 52 and a tapered plate 54, a cooling chamber spacer 56 for providing a cooling chamber, and a rear end plate 58. A first gasket 60 separates the front end plate 50 from the separation chamber spacer 52 and a second gasket 62 separates the rear end plate 58 from the cooling chamber spacer 56. The separation chamber spacer 52 comprises buffer inlet ports 64 for introducing a separation buffer and at least one sample port 66 for introducing a sample.

A plurality of conduits 68 are vertically disposed through the side surfaces of the separation chamber spacer 52 to allow for electrical continuity and sample entry. Sample outlet ports 70 are located on a front side surface of the separation chamber spacer 52 and buffer outlet ports 72 are located along the bottom side of the separation chamber spacer 52. The conduits 68 in the side of the separation chamber spacer 52 and the sample outlet ports 70 in the front side of the separation chamber spacer 52 combine to form a plurality of cross flow fraction collectors 74. The front end plate 50, the first gasket 60, the tapered plate 54, the cooling chamber spacer 56, the second gasket 62, and the rear end plate 58 also contain sample outlet ports 70 so that sample can pass through the layers of the apparatus and be collected at a point external to the apparatus.

To employ the apparatus, the front end plate 50, the first gasket 60, the separation chamber spacer 52, the tapered plate 54, the cooling chamber spacer 56, the second gasket 62, and the rear end plate 58 are sandwiched together and held in place by screws 76 and nuts 78. An electrode chamber assembly 80 is then attached to the separation chamber spacer 52 to impart an electrical field across the separation chamber. The electrode chamber assembly 80 comprises an electrode compartment 86 and a third gasket 82 which frames an ion exchange membrane 84. Positive and negative electrode chamber assemblies 80 are positioned on the outer side walls 88 of the separation chamber spacer 52, respectively.

Next, a coolant reservoir and pump are connected to the coolant chamber spacer 56 via a coolant inlet port 90 and a coolant outlet port 92. A separation buffer is introduced into the closed tapered chamber via the buffer inlet ports 64 and recirculated through the separation chamber via buffer reservoir inlet and outlet ports 94, 96 located in the electrode compartments 86 of the electrode chamber assemblies 80. Following this connection, at least one sample is introduced into the sample inlet port 66 via an injection needle. The positive and negative electrode chamber assemblies 80 are then connected to a power supply to impart an electric field across the separation chamber to enable the separation of the sample whose components are then collected in the cross flow fraction collector 74. The collected sample components then exit the electrophoresis apparatus through the sample outlet ports 70 with the help of a multichannel pump. This configuration of the electrophoresis apparatus functions to enhance the peak to peak distance between the sample's separated components.

Figure 15B:
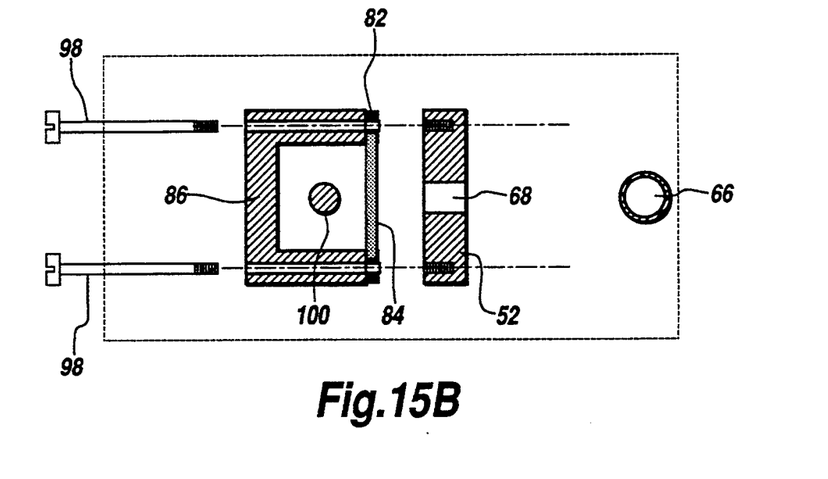

A cross-sectional view of the upper portion of the separation chamber and electrode chamber assembly 80 is shown in FIG. 15b. The electrode compartment 86 is connected to the third gasket 82, which frames an ion exchange membrane 84, which is in turn connected to the separation chamber spacer 52. The connection of these components is maintained via screws 98. The negative electrode is contained within the center of the electrode compartment 86. Conduit 68 carries separation buffer from the separation chamber to the ion exchange membrane 84. Conduits 68 provide for electrical continuity during the electrophoresis process.

Figure 15C:
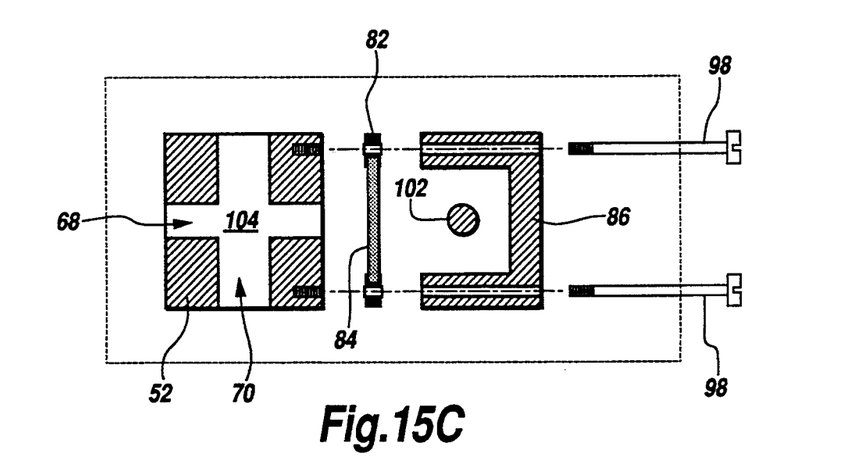

FIG. 15c depicts a cross-sectional view of a lower portion of the separation chamber and electrode chamber assembly 80. The electrode compartment 86 which contains the positive electrode 102 is connected to the third gasket 82 which frames an ion exchange membrane 84. The third gasket 82 is then connected to the separation chamber spacer 52. Like the upper portion of the separation chamber and electrode chamber assembly described above, the connection of these components is maintained via screws 98. The separation chamber spacer 52 comprises a cross flow fraction collector 104 which results from the crossing of a conduit 60 with a sample outlet port 70. A sample component is collected by entering through conduit 60. The sample component is then drawn out from the cross flow fraction collector 104 through outer sample port 70 via a multichannel pump which directs the sample component into a tube.

Figure 16:
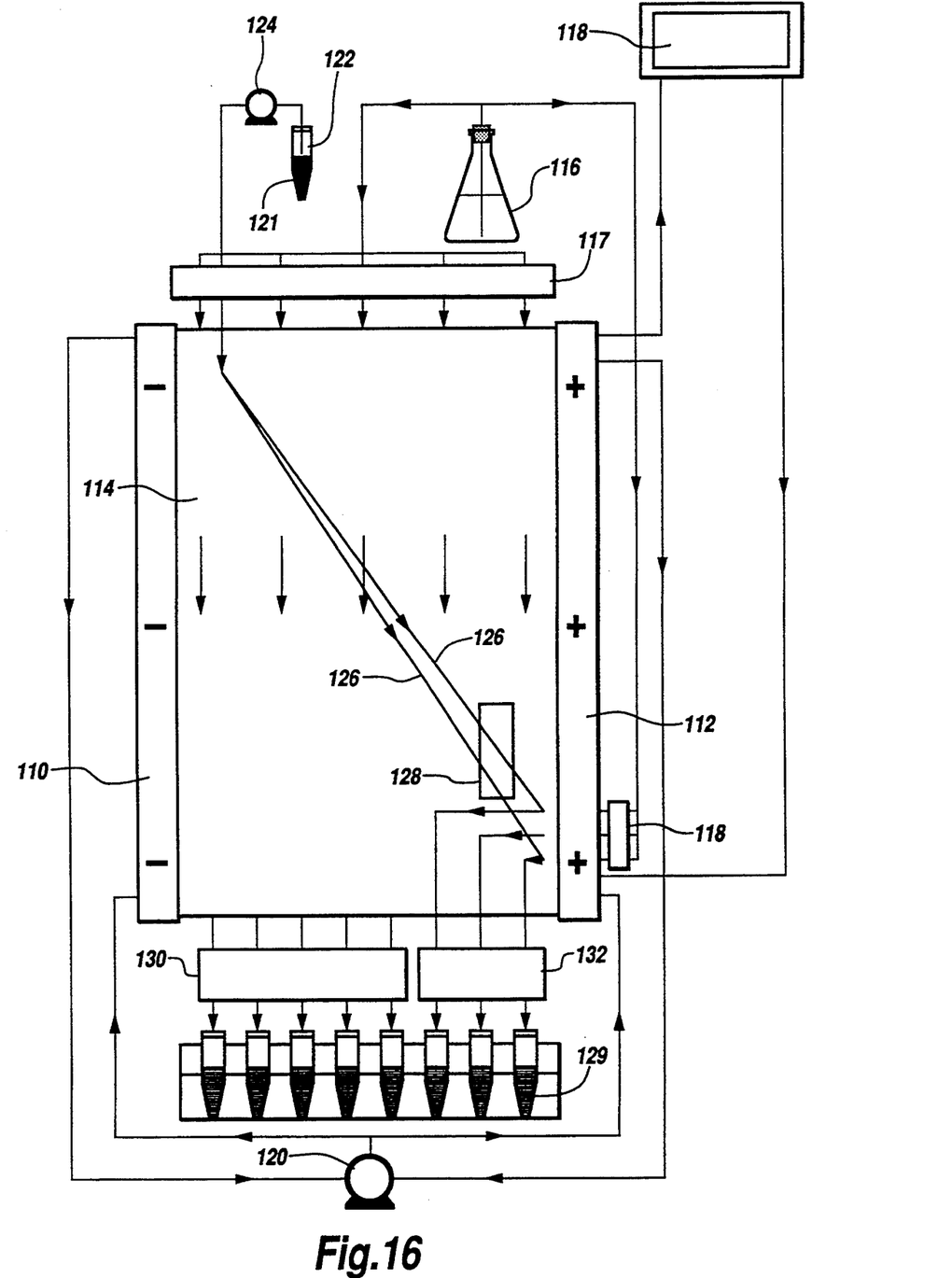

Finally, a diagrammatic view of the modified continuous flow zone electrophoresis is illustrated in FIG. 16. A negative electrode component 110 and a positive electrode component 112 are located on opposite sides of a separation chamber 114 to impart an electric field across the separation chamber 114. A separation buffer is introduced into the separation chamber from a separation reservoir 116 via a first multichannel pump 117. The separation buffer is recirculated through the separation chamber 114 via a second multichannel pump 118.

The separation chamber is cooled by a coolant which originates from a chiller 118 which contains a pump and a reservoir for the coolant. The coolant recirculates through the electrode chambers 110, 112 via an electrode pump 120 to keep the separation chamber 114 cooled. A sample 121 is introduced from a sample reservoir 122 into the separation chamber 114 via a sample pump 124 which injects the sample into the separation chamber 114. The sample is separated in the separation chamber 114 into sample components 126. The sample components are detected by an optical detector 128 and then drawn into a cross flow fraction collector.

Output separation buffer is collected into fraction collector tubes 129 via a third multichannel pump 130 and sample components are collected from the cross flow fraction collector via a fourth multichannel pump 132. Sample components can then be drawn from the fraction collector tubes 129 and tested.

Thus, the invention has been described in accordance with the preferred embodiments thereof. Those skilled in the art will understand that various chamber configurations, sample compositions, buffer components and applied field strengths, are contemplated as being within the spirit and scope of the present invention, so long as the residence time of one component is selectively enhanced over that of a slower component in the sample.

We claim:

1. A method of continuous flow zone electrophoresis, comprising the steps of:
   a) introducing a sample containing at least two populations of charged components into a buffer fluid;
   b) flowing the buffer fluid containing the sample into a separator chamber; and
   c) selectively increasing a residence time of a faster charged component over a slower charged component within the chamber and separating said faster charged component from said slower charged component by imposing a negative gradient in bulk fluid velocity along a direction of the electrophoresis.

2. The method according to claim 1, wherein said step of selectively increasing a residence time further comprises the steps of orienting a fraction collector in axial alignment with said flow of said buffer fluid containing the sample and collecting said separated components said axially oriented fraction collector.

3. The method according to claim 1, wherein said step of selectively increasing a residence time further comprises the step of reorienting said applied field such that said field is co-axial with a fluid flow velocity profile within the separation chamber.

4. The method according to claim 1, wherein said step of flowing the buffer fluid containing the sample further comprises the step of flowing said sample in a first direction.

5. The method according to claim 4, wherein said step of flowing said buffer fluid containing the sample in a first direction comprises flowing said buffer fluid containing the transverse to a direction of said applied field.

6. The method according to claim 1, further comprising the step of collecting said separated components in a fraction collector oriented axially with a direction of said flow of said buffer fluid containing the sample.

7. The method according to claim 6, wherein said step of flowing a sample into a separator chamber further comprises flowing the sample into a tapered chamber.

8. The method according to claim 6, wherein said step of flowing a sample into a separator chamber further comprises flowing the sample into an annular chamber and said step of collecting said separated components comprises collecting said components in a fraction collector residing within an annular opening of said annular chamber.

9. The method according to claim 6, wherein said step of collecting said separated components further comprises collecting said separated components in a fraction collector having a tapered electrode contained within said separation chamber and opposingly positioned to said fraction collector such that a tapered collection chamber is formed therebetween.

10. An apparatus for continuous flow zone electrophoresis, comprising:
a fluid flow chamber having an upper and lower aspect thereof and side walls defining an interior fluid flow opening;
a fraction collector operably associated with a side wall and in close proximity to said lower aspect of said fluid flow chamber, said fraction collector being in fluid flow communication with said interior fluid flow opening;
means for generating a field across said fluid flow chamber; and
at least one of means for generating a field through said fraction collector so as to draw out at least one separated sample fraction and suctioning means for suctioning at least one separated sample fraction, said suctioning means being in fluid flow communication with said fraction collector.

11. The apparatus according to claim 10, wherein said fluid flow chamber further comprises a generally quadrilateral cross-section.

12. The apparatus according to claim 10, wherein said fluid flow chamber further comprises a generally tetrahedral cross-section.

13. The apparatus according to claim 10, wherein said fluid flow chamber further comprises an annular cross-section.

14. The apparatus according to claim 11, wherein said means for generating a field is oriented to generate a field across a longitudinal aspect of said fluid flow chamber.

15. The apparatus according to claim 11, wherein said means for generating a field is oriented to generate a field across a lateral aspect of said fluid flow chamber.

16. The apparatus according to claim 13, wherein said means for generating a field is oriented to generate a radial field across said fluid flow chamber.

17. The apparatus according to claim 10, wherein said suction means comprises a multichannel pump.

18. The apparatus according to claim 12, wherein said side walls are in a non-parallel relationship and at least one of said side walls is co-axial with said fluid flow.

19. A method of continuous flow zone electrophoresis, comprising the steps of:
a) introducing a sample of at least two populations of charged components into a buffer fluid;
b) flowing the buffer fluid containing the sample into a separator chamber; and
c) selectively increasing an electrophoretic migration rate of a faster charged component over a slower charged component within the chamber and separating said faster charged component from said slower charged component by flowing the buffer fluid containing the sample into a positive gradient in the applied field strength along a direction of the electrophoresis.

20. The method according to claim 19, wherein said step of flowing the buffer fluid containing the sample further comprises the step of flowing the buffer fluid containing the sample in a first direction.

21. The method according to claim 20, wherein said step of flowing the buffer fluid containing the sample in a first direction comprises flowing said buffer fluid containing the sample transverse to a direction of said applied field.

22. The method according to claim 19, further comprising the steps of collecting said separated components in a fraction collector oriented axially with a direction of said flow of the buffer fluid containing the sample.

23. The method according to claim 22, wherein said step of flowing the buffer fluid containing the sample into said separation chamber further comprises flowing the buffer fluid containing the sample into a tapered chamber.

24. The method according to claim 22, wherein said step of flowing the buffer fluid containing the sample into said separation chamber further comprises flowing the buffer fluid containing the sample into an annular chamber, and said step of collecting said separated components comprises collecting said components in a fraction collector residing within an annular opening of said annular chamber.

25. The method according to claim 22, wherein said step of collecting said separated components further comprises collecting said separated components in a fraction collector having a tapered electrode contained within said separation chamber and opposingly positioned to said fraction collector such that a tapered collection chamber is formed therebetween.

* * * * *